United States Patent
Bhattacharya et al.

(10) Patent No.: US 12,383,902 B2
(45) Date of Patent: Aug. 12, 2025

(54) LOW COST MICROFLUIDIC DEVICE FOR DNA/RNA ISOLATION, PURIFICATION AND AMPLIFICATION USING CHIP BASED PCR/RT-PCR FOR BIOSENSING APPLICATIONS

(71) Applicant: Jaydeep Bhattacharya, New Delhi (IN)

(72) Inventors: Jaydeep Bhattacharya, New Delhi (IN); Rajkamal Bharti, Moradabad (IN); Asha Ashwathi Madhavan, Vidyanagar (IN); Ranjita Ghosh Moulick, Asansol (IN)

(73) Assignee: Jaydeep Bhattacharya, New Delhi (IN)

( * ) Notice: Subject to any disclaimer, the term of this patent is extended or adjusted under 35 U.S.C. 154(b) by 1125 days.

(21) Appl. No.: 16/968,416

(22) PCT Filed: Feb. 5, 2019

(86) PCT No.: PCT/IN2019/050090
§ 371 (c)(1),
(2) Date: Aug. 7, 2020

(87) PCT Pub. No.: WO2019/155488
PCT Pub. Date: Aug. 15, 2019

(65) Prior Publication Data
US 2020/0398274 A1    Dec. 24, 2020

(30) Foreign Application Priority Data
Feb. 7, 2018  (IN) .............................. 201811004666

(51) Int. Cl.
*B01L 3/00* (2006.01)
*B01L 7/00* (2006.01)
(Continued)

(52) U.S. Cl.
CPC ......... *B01L 3/502792* (2013.01); *B01L 7/525* (2013.01); *C12Q 1/6806* (2013.01);
(Continued)

(58) Field of Classification Search
CPC ..................................................... B01L 7/525
See application file for complete search history.

(56) References Cited

U.S. PATENT DOCUMENTS

2009/0186357 A1* 7/2009 Mauk .................... B01L 3/5027
435/6.15
2009/0263870 A1* 10/2009 Pipper .................... C12P 19/34
435/91.2

(Continued)

FOREIGN PATENT DOCUMENTS

DE    69734587 T2    7/2006
EP    3168287 A1     5/2017
WO    2017/043893 A1  3/2017

OTHER PUBLICATIONS

Pipper, J. et al. "Clockwork PCT Including Sample Preparation," Angew. Chem. Int. Ed. 2008, 3900-3904 (Year: 2008).*
(Continued)

*Primary Examiner* — Jennifer Wecker
*Assistant Examiner* — Michelle Adams
(74) *Attorney, Agent, or Firm* — Hamilton, Brook, Smith & Reynolds, P.C.

(57) ABSTRACT

The present invention relates to a low cost microfluidic device for DNA/RNA isolation, purification and amplification using Chip based PCT/RT-PCR for the development of optical, electrochemical, magnetic and other biosensing applications. It relates to isolation and purification of DNA/RNA inside microfluidic device using in-channel anodized alumina nanopores or any other nanoporous membrane and amplification of DNA on low voltage resistive heater based spatial PCR Chip where the three temperature zones have (Continued)

Figure 1:
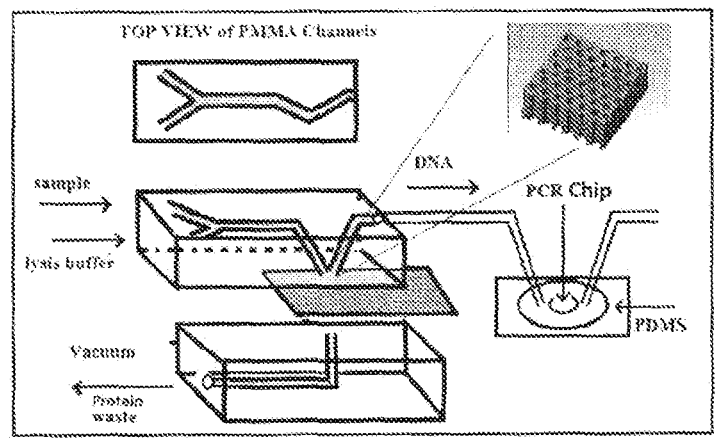

been generated and placed as the vertices of an equilateral triangle. This portable DNA isolation and amplification device can be integrated to any type of Biosensors and even it can act as point of care device for the detection of pathogens including biological warfare agents or any other genetic diseases which can be detected through PCR.

14 Claims, 4 Drawing Sheets

(51) Int. Cl.
    *C12Q 1/6806*     (2018.01)
    *C12N 15/10*     (2006.01)

(52) U.S. Cl.
    CPC . *B01L 3/502707* (2013.01); *B01L 2300/0681* (2013.01); *B01L 2300/0896* (2013.01); *B01L 2300/1827* (2013.01); *B01L 2400/043* (2013.01); *C12N 15/1017* (2013.01)

(56) References Cited

U.S. PATENT DOCUMENTS

| | | |
|---|---|---|
| 2011/0244467 A1 | 10/2011 | Haswell |
| 2012/0088234 A1* | 4/2012 | Hartwich .............. B01L 7/5255 435/6.12 |
| 2015/0283514 A1* | 10/2015 | Aguilar .................. B01D 71/02 156/182 |
| 2016/0265032 A1 | 9/2016 | Sethi et al. |
| 2016/0288121 A1 | 10/2016 | Ismagilov et al. |
| 2017/0028402 A1 | 2/2017 | Hishida |
| 2017/0051344 A1 | 2/2017 | Goyal et al. |

OTHER PUBLICATIONS

You, D.J. et al. "Very quick reverse transcription polymerase chain reaction for detecting 2009 H1N1 influenza A using wire-guide droplet manipulations," Faraday Discuss., 2011, 149, 159-170 | (Year:2011).*

Sun, Y. et al. "A circular ferrofluid driven microchip for rapid polymerase chain reaction," Lab Chip, 2007, 7, 1012-1017 (Year: 2007).*

Xu, Z.-R. et al. "An extrusion fluidic driving method for continuous-flow polymerase chain reaction on a microfluidic chip," Microchim Acta (2010) 168:71-78 (Year: 2010).*

Kim, J. et al. "Quantitative and qualitative analysis of a microfluidic DNA extraction system using a nanoporous AlOX membrane," Lab Chip, 2008, 8, 1516-1523 (Year: 2008).*

PCT International Search Report and Written Opinion for International Application No. PCT/IN2019/050090, entitled "A Low Cost Microfluidic Device for DNA/RNA Isolation, Purification and Amplification Using Chip Based PCR/RT-PCR for Biosensing Applications," mailed on May 17, 2019.

* cited by examiner

LOW COST MICROFLUIDIC DEVICE FOR DNA/RNA ISOLATION, PURIFICATION AND AMPLIFICATION USING CHIP BASED PCR/RT-PCR FOR BIOSENSING APPLICATIONS

This application is the U.S. National Stage of International Application No. PCT/IN2019/050090, filed Feb. 5, 2019, which designates the U.S., published in English, and claims priority under 35 U.S.C. § 119 or 365 (c) to Indian Application No. 201811004666, filed Feb. 7, 2018. The entire teachings of the above applications are incorporated herein by reference.

The present invention relates to a low cost microfluidic device for DNA/RNA isolation, purification and amplification using Chip based PCR/RT-PCR for the development of optical, electrochemical, magnetic and other biosensing applications. It relates to isolation and purification of DNA/RNA inside microfluidics using in-channel anodized alumina nanopores and amplification of DNA on low voltage resistive heater based spatial PCR Chip where the three temperature zones have been generated and placed as the vertices of an equilateral triangle.

BACKGROUND OF THE INVENTION

In 2015 some workers have tried Nucleic acid amplification device which was comprised of heaters to form denaturation temperature zone and an extension or annealing zone. Movement of sample solution was detected by a fluorescence detector. They also provided liquid delivery stop and a mechanism that controls driving of each liquid delivery by receiving electrical signal from fluorescence detector according to movement of the sample solution in real time for each thermal cycle. [1]

In 2016, a patent was filed for PCR based point-of-care testing device, comprising of a container fastened to the cap, the upper portion of the container for the Testing device having a micro fluidic coupled with electrophoresis. [2]

In 2016, some workers tried to develop a portable DNA Analysis Machine in which the system can include a containment chip capable of holding a sample and reagents for amplifying a nucleic acid in the sample and containing a unique identifier used to choose a nucleic acid amplification protocol. The system can also include a nucleic acid detection component which may contain a light source, a light sensor, a temperature control unit and a processor. [5]

Recently in 2017, some workers have developed microfluidics chip based purification device and a system for Sanger-sequencing reactions. The micro fluidics chip described can be used as a PCR chip by reorganizing the on-chip reagents, reaction wells and work flow steps. [3]

Some workers also developed a micro-channel chip, PCR method, and heating or cooling control apparatus, i.e. a method for PCR on a treatment target liquid using a micro-channel chip and a heating or cooling control apparatus is provided. The micro-channel chip includes a $1^{st}$ substrate layer and $2^{nd}$ substrate layer that is disposed on the first substrate layer and a metal film structuring an upper surface of micro-channel. Their heating/cooling control apparatus includes a temp regulator, and a power source that supplies voltage to temp regulator. Heating/cooling controllers that controls heating or cooling of the temp regulator by controlling voltage. The heat of the temperature regulator is conducted to the liquid in the micro channel via metal film. [4] The main obstacle for any DNA/RNA based diagnostic system is the isolation of DNA/RNA from samples. In the present invention, the inventors have designed a nano-channel based microfluidic device that can isolate the nucleic acids in one step. The device of the present invention involves isolation and purification of DNA/RNA inside microfluidics using in-channel anodized alumina nanopores and amplification of DNA on low voltage resistive heater based spatial PCR Chip where the three temperature zones have been generated and placed as the vertices of an equilateral triangle.

SUMMARY OF THE INVENTION

The present invention relates to a low cost microfluidic device for DNA/RNA isolation, purification and amplification using Chip based PCR/RT-PCR, for the development of optical, electrochemical, magnetic and any other biosensing applications.

One embodiment of the present invention relates to a nano-channel based microfluidic device that can isolate the nucleic acids in one step. In this embodiment, the device is a two input microfluidic device. From one input channel the cells, Serum, or Bacteria/Virus contaminated fluid is injected and the lysis buffer is injected through the other.

In the other embodiment, the isolation and purification of DNA/RNA is inside the microfluidics using in-channel anodized alumina nanopores or any other nanoporous membrane.

Another embodiment of the present invention relates to amplification of the isolated and purified DNA by portable PCR or portable chip based PCR.

In the other embodiment of the present invention, amplification of DNA is carried out on low voltage resistive heater based spatial PCR Chip where the three temperature zones have been generated and placed as the vertices of an equilateral triangle.

In the other embodiment of the present invention, chip contains circuit design for 3 different temperature zones. In this embodiment, the chip is TEFLON™ (polytetrafluoroethylene (PTFE)) coated so as to keep minimum ground friction for the sample drop. Chip is directly connected to the temperature controllers and held at an elevated platform. It requires very less voltage and the required potential can be supplied from the battery In another embodiment, the dimension of the chip is 2 cm by 2 cm which can be reduced.

In another embodiment, the chip may be designed in the way so that multiple PCR reaction can be performed simultaneously.

Another embodiment of the present invention relates to the on-chip PCR module that has been equipped with a detection unit. The DNA amplification can be quantified by using standard SYBR™ green dye (DNA binding fluorescent dye).

Another embodiment of the present invention includes running of the PCR device using the Stepper motor guided neodymium magnets.

In the other embodiment the droplet containing the PCR mix required for the DNA amplification is mixed with magnetic nanomaterials so that the movement of the droplet can be controlled by the mentioned magnet.

In the other embodiment of the present invention, Arduino microcontroller is used to guide the movement of neodymium magnets and sample drop henceforth. A freeware programming code was modified as per the need of PCR protocol. Speed control with time delay was done with the help of standard programming code developed.

BRIEF DESCRIPTION OF THE ACCOMPANYING FIGURES

FIG. 1: Schematics of the proposed microfluidic device.

Figure 2:
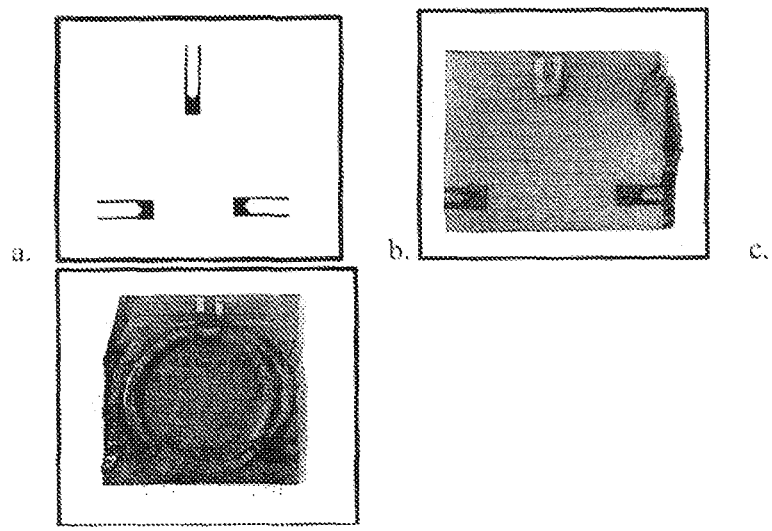

FIG. 2: The figure depicts a. the image of the mask used b. the fabricated chip on the PCB c. the chip containing the reaction chamber.

Figure 3:
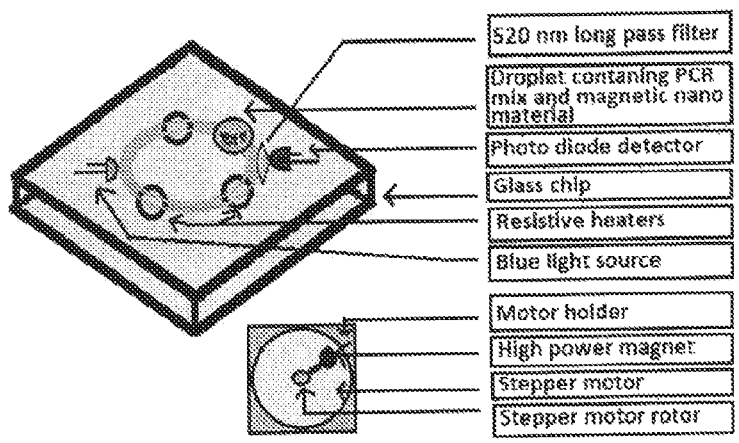

FIG. 3: Schematic of the droplet PCR on chip with the description of the individual components.

Figure 4:
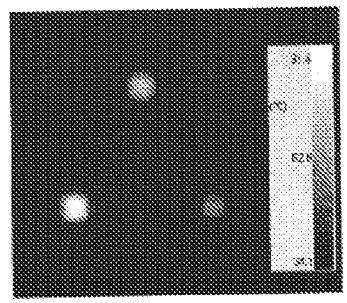

FIG. 4: Design of the chips and the thermographic images of the heaters when heated to the requisite temperatures by applying voltages.

Figure 5:
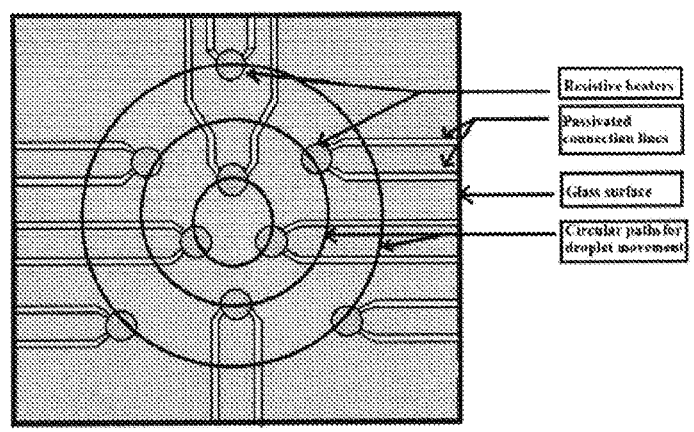

FIG. 5: Schematic diagram of the chip where PCR of multiple samples can be performed at the same time.

Figure 6:
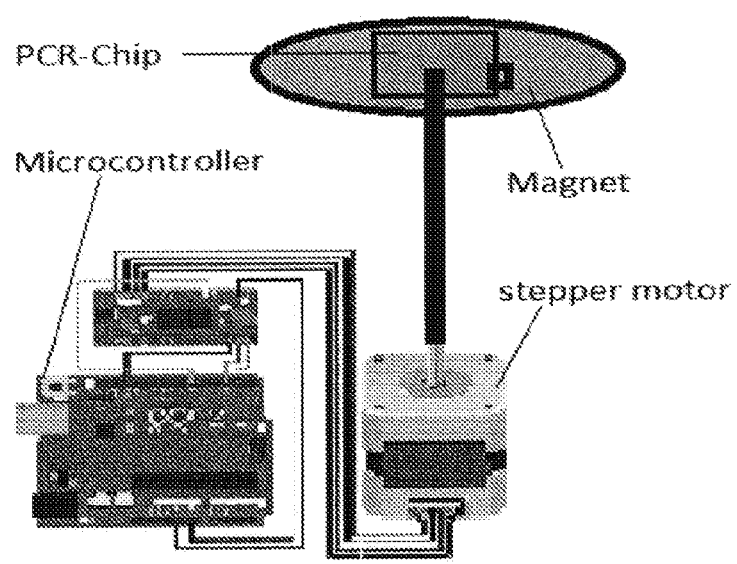

FIG. 6: Schematic diagram of the Aurdino microcontroller controlled stepper motor for the mobilization of the droplet containing based magnetic nanoparticles.

Figure 7:
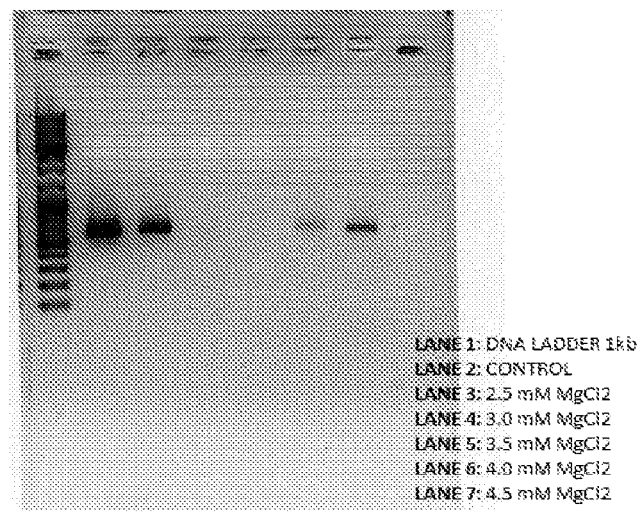

FIG. 7: Agarose gel image of the PCR products at higher Mg concentration.

DETAILED DESCRIPTION OF THE INVENTION

The present invention relates to a low cost microfluidic device for DNA/RNA isolation, purification and amplification using Chip based PCR/RT-PCR for the development of optical, electrochemical, magnetic and other biosensing applications (FIG. 1).

Design & Principle:

Isolation of DNA/RNA Inside Microfluidics Using on Chip Anodized Nano Porous Alumina Membrane The main obstacle for any DNA/RNA based diagnostic system is the DNA/RNA isolation from the samples. In the present invention, the inventors have designed a nano-channel based microfluidic device that can isolate the nucleic acids in one step.

In one embodiment, the device of the present invention involves isolation and purification of DNA/RNA inside microfluidics using in-channel anodized alumina nanopores and amplification of DNA on low voltage resistive heater based spatial PCR Chip where the three temperature zones have been generated and placed as the vertices of an equilateral triangle. The microfluidics device is a specially designed sandwiched model where the aluminium is placed at the junction and has been anodised to form nano channels. Any other nano-porous membrane can be used for this purpose.

In a particular embodiment, the device is a two input microfluidic device. From one input channel, the cells, Serum or Bacteria/Virus contaminated fluid is injected and the lysis buffer is injected through the other. The DNA/RNA from any cell lysate or any bacteria/virus containing fluids can be isolated by this process where the protein nucleic acid mixture after the lysis is subjected to a filtration unit made of anodized alumina nano-channels inside microfluidic device. The pores have been fabricated by the process of in-channel anodization of aluminium foil or any other nanoporous material placed between the specially designed sandwiched microfluidic channels.

Anodization of the Aluminium Sheets Inside Microfluidics Channel

Small square Aluminium sheets were placed at the junction of the two chambers and anodized using 0.3 M oxalic acid. The power supply was setup and the Aluminium foil was used as the anode, whereas a small platinum wire was used as the cathode. The setup was run at constant voltage of 50 V and the current ranged from 0.1 mA to 0.4 mA for a time period of 15-20 minutes. The nanoporous septum was thus prepared and the residual aluminium layer was removed by etching, using 0.1 M phosphoric acid.

Isolation of Nucleic Acids Using the Nanoporous Membrane

1 µg/ml genomic DNA and 1 mg/ml of the protein solution of Bovine Serum Albumin (BSA) were prepared in 1× Phosphate buffer saline of pH 7.4 (PBS). 10 uL of the Genomic DNA stock and 10 uL of the BSA stock were mixed in a microcentrifuge tube and volume was made up to 100 uL using PBS. The ratio of the absorbance at 260 nm to 280 nm (A260/280) of DNA-Protein mix was measured spectrophotometrically. The solution was passed through the anodized aluminium and the filtrate was collected at the bottom chamber. The A260/280 of this filtrate and the solution that remained at the top chamber was measured spectrophotometrically and the data has been summarized in Table 1.

TABLE

1 One Step DNA and Protein Separation using Nanopores

| | A260/A280 | DNA CONC. (ng/ul) | A 260 nm for DNA | A 280 nm for protein |
| --- | --- | --- | --- | --- |
| AFTER passing through the nanopores (LOWER chamber) | 0.589<br>0.604 | 6.8<br>4.55 | 3.416<br>0.922 | 5.754<br>1.524 |
| AFTER passing through the nanopores (UPPER chamber) | 1.432<br>1.444 | 167.80<br>145.850 | 0.137<br>0.092 | 0.096<br>0.064 |

Preparation of Standard 1×PBS of pH 7.4:
1. Take 800 mL of distilled water in a suitable container.
2. Add 8 g of NaCl to the solution.
3. Add 200 mg of KCl to the solution.
4. Add 1.44 g of $Na_2HPO_4$ to the solution.
5. Add 240 mg of $KH_2PO_4$ to the solution.
6. Adjust the pH of solution to 7.4.
7. Add distilled water to make up the volume to 1 L.

The nucleic acid gets purified as the protein passes through the pores of the nano-channel and gets collected as a waste material. The purified DNA/RNA was subjected to PCR using predesigned primers.

The other embodiment of the present invention includes the next step after the DNA/RNA isolation, which is amplification by PCR. Chip based PCR or portable PCR is a need of the hour owing to its importance in majority of the research involving molecular biology of diseases. To develop a real-time PCR and also portable one, can be of great significance in various applications like diagnosis of DNA/RNA based infectious microbial diseases, detecting circulatory tumour cells and even in forensic investigations. Generally, it has been found that sample is carried from the place of evidence to the lab, and in the process it leads to deterioration or contamination of the samples. So, it would be a good practice to develop portable PCR to amplify the sample at the place of evidence itself.

Many workers have tried similar approaches but a distinct compact and efficient micro-system is still needed.

In one of the embodiment of the present invention, the inventors' approach is to employ cost effective methods for the development of portable chip based PCR.

Fabrication of the PCR Chip (FIG. 2)
Photolithography on Copper Coated Printed Circuit Board (PCB):
Step 1: Washing
  i. Rinse the PCB with the gentle soap like hand wash.
  ii. Wash thoroughly with absolute Ethanol.
  iii. Wipe off any liquid remaining using a lint-free tissue paper.
  iv. Dry the PCB in an Hot air Oven (5 min at 55° C.)).
Step 2: Photoresist Coating
  i. Using a micropipette, coat photoresist onto the PCB using a spin coater in such a way that a uniform thin layer is formed (Here the inventors used a positive photoresist).
  ii. Spin the PCB immediately after applying photoresist at 2000 rpm for 1 minute.
Step 3: Soft Baking
  i. Bake the PCB on the hot plate at 95° C. ° C. for 4 minutes.
  ii. Bake the PCB in the hot air oven at 60° C.° C. for 4 minutes.
Step 4: Mask Alignment & Exposure
  i. Place Photomask on the PCB.
  ii. After this, expose the PCB under UV (311 nm) source for 4 minutes.
Step 5: Development
  i. Use NaOH as the developing solution.
  ii. First develop using 0.4% NaOH & 0.5% NaOH.
  iii. Use 1% NaOH for removing the photoresist from the edges of the PCB.
  iv. After this, wash with MILLI-Q™ water to remove the excess of NaOH.
Step 6: Hard Baking
  i. Bake the PCB in hot air oven at 60°e° C. for 15 minutes.
Step 7: Etching
  i. Using 60% $FeCl_3$ etch the copper from the PCB.
  ii. The photoresist coated portion of PCB would not be removed.
Step 8: Striping
  i. Remove the photoresist using absolute ethanol.
  ii. This would give us the desired pattern we want to obtain.

The mask, the electrodes after the fabrication and the electrodes having the glass ring forming the reaction chamber has been shown in FIG. 2.

Quantitative Droplet PCR for DNA Amplification on Chip

Another embodiment of the present invention includes a Chip, which has been designed where polymerase chain reaction can be done. In a particular embodiment, unlike the conventional PCR where temperature is changed over time for every cycle, this chip has three stable temperature zones (FIG. 4) There are other PCR chips also but they use external heaters for the thermal cycle. But this new PCR chip has in-house resistive heaters that on application of definite voltage maintain the required temperature for PCR as shown in FIG. 5. The heaters are fabricated on the chip surface as the vertices of an equilateral triangle. As the circumcircle touches the vertices the droplet when moved on the surface in a circular motion, the PCR mix inside the droplet can experience the temperature and the PCR is done. The voltage ranges from 2V to a maximum of 20 V for the generation of the three temperature zones depending on the fabrication process. The mixture is moved by adding magnetic nanoparticles in it and by placing a magnet coupled with a motor at the bottom of the chip (FIG. 6).

PCR in Presence of Magnetic Nanoparticles on the Chip
  Magnetic nanoparticles were synthesized using co-precipitation method.
  This particles were autoclaved.
  This particles were mixed with the PCR reaction mix.
  PCR products in presence of these nanoparticles were obtained after increasing the concentration of $MgCl_2$.
  PCR reactions were carried out with increasing concentration of $MgCl_2$ ranging from 2.5 mM to 4.5 mM (normal PCR reaction is at 2 mM $MgCl_2$).
  The Results obtained are shown in FIG. 7.
Preparation of PCR Sample (Standard Method)
  1. Isolate the plasmid/genomic DNA.
  2. Prepare PCR sample by adding 1 uL of forward primer, 1 uL of reverse primer, 25 uL of master mix x uL of DNA (x depends on concentration of DNA in PCR sample this should be 60-80 ng/uL), make up the volume up to 50 uL using Nuclease Free Water (NFW).
  3. Prepare the PCR sample with magnetic nanoparticles and an additional concentration of $MgCl_2$ with the components described in step 2. (PCR reactions were carried out with increasing concentrations of $MgCl_2$ ranging from 2.5 mM to 4.5 mM (normal PCR reaction is carried out at 2 mM $MgCl_2$).
  4. Run PCR using condition suitable for the PCR reaction.
  5. After this run agarose gel electrophoresis and observe this under UV light (FIG. 7).
Agarose Gel Electrophoresis (Standard Method)
  1. Make 1 L of 1×Tris Acetate EDTA (TAE) Buffer (20 mL of 50×TAE into 1 L MILLI-Q™ Water).
  2. Pour 100 mL of 1×TAE into a clean 250 mL flask. Add 0.8 g of Agarose into 100 mL 1×TAE to make 0.8% gel (w/v), or 1 g for a 1% gel. Microwave until the solution is clear, and just starts to bubble. Cool down the agarose solution for 5 minutes.
  3. Add Ethidium Bromide (EtBr) to a final concentration of 0.05 µg/mL (For a 100 mL gel add 5 µL from 10 mg/mL stock).
  4. Pour the warm liquid agarose onto the gel casting tray and place the comb into the casting tray by placing the sides into the notches.
  5. Wait until the gel polymerizes. It usually takes about an hour. The gel should look opaque and uniform.
  6. Fill the Gel Tank with 1×TAE.
  7. Remove the gel combs and load molecular weight marker in one lane.
  8. Add loading dye (final concentration of 1× loading dye) to the samples and load the samples into the wells.
  9. Plug in the gel unit and run the gel at 50V for about 90 min.
  10. Visualize DNA gel under UV light.
Preparation of 6× Loading Dye:
  0.25% Bromophenol blue (BB) (or tiny amount on the spatula tip), 0.25% Xylene cyanol (FF XC) (or same as BB), 15% Ficoll, 120 mM EDTA (240 µL of 0.5 M EDTA in 1 mL to make a 6× loading dye)
Preparation of 50×TAE:
  242 g Tris-base, 57.1 mL Acetic Acid glacial, 100 mL 0.5 M EDTA In the other embodiment of the present invention, the on-chip PCR module has been equipped with a detection unit. So the DNA amplification can be quantified by using standard SYBR™ green dye. A blue light source (emission band 470-490 nm) is coupled to the chip and a photo diode detector with a 520 nm long pass filter for the optical quantification of the amplified DNA (FIG. 4).

It is an open device to avoid the evaporation of the droplet, silicon oil was used to immerse the droplet. The inventors have used Magnetic Nanoparticle assembly to guide and pull the DNA sample drop through the silicon oil. To minimize the friction of the droplet containing the PCR mixture, the inventors have also coated the chip with the commercially available TEFLON™ spray.

In another embodiment of the invention, in order to keep the optimum condition for PCR, that is continuous rotation with 3 short duration stops, the arduino programme was designed. Rotating magnet was fixed on the lower platform which was connected to stepper motor, which in turn was controlled by Arduino microcontroller (FIG. 6).

Schematic:

As mentioned in the above paragraphs, the inventors have designed a single chip with 3 different temperature zones. Temperature of these zones is stable and maintained by applying fixed potential. Sample is encapsulated in the aqueous drop containing magnetic nanoparticles. Magnetic force from the rotating neodymium magnets is the driving force for aqueous sample drop through the different temperature zones. Optimization of stopping time over each zone is fixed according to DNA replication protocol.

Chip:

In one embodiment of the present invention, chip contains circuit design for 3 different temperature zones. In a particular embodiment, chip is TEFLON™ coated so as to keep minimum ground friction for the sample drop. Chip is directly connected to temperature controllers and held at elevated platform. It requires very less voltage and the required potential can be supplied from the battery.

In another embodiment, the dimension of the chip is 2 cm by 2 cm, which can be reduced.

In other embodiment, the chip may be designed in the way so that multiple PCR reaction can be performed simultaneously.

In other embodiment of the present invention, the chip is designed on the basis of creating three temperature zones placed at the vertices of an equilateral triangle where the circumcircle can touch the vertices for performing the PCR. Several concentric circles with different diameter can be made where the samples can move on the temperature zones without any interaction and mixing (FIG. 5). In the figure a design has been given where the PCR of the three samples can be done simultaneously. It may be more. This is just an example.

Stepper Motor Guided Neodymium Magnets:

In another embodiment, stepper motor is fixed below the elevated platform. Its shaft is connected to the iron sheet having neodymium magnets attached to the sheet.

Softwares:

The other embodiment relates to Arduino microcontroller, which is used to guide the movement of neodymium magnets and sample drop henceforth. A freeware programming code was modified as per the need of PCR protocol. Speed control with time delay was done with the help of standard programming code developed.

INDUSTRIAL APPLICABILITY

The potential application of the present invention is in developing a microfluidic device for in-channel isolation and amplification of target gene. The digital droplet PCR chip of the present invention is the cost effective standalone PCR device. The whole device is a unique of its type that can isolate and quantitatively amplify the DNA inside the microfluidic channels. As the droplet is moved spatially on the preheated temperature zones, it is the fastest PCR available.

It does not require any time to change the temperature and is independent of the rate of temperature change of the heating units.

This portable DNA isolation and amplification device can be integrated to any type of Biosensors and even it can act as point of care device for the detection of pathogens including biological warfare agents or any other genetic diseases which can be detected through PCR.

REFERENCES

1. Patent No. EP3168287/15818467
2. Patent No. WO/2017/043893/PCT/KR2016/010111
3. Patent No. US20170051344/15113786
4. Patent No. US20170028402/15183298
5. Patent No. US20160265032/15068050

We claim:

1. A system, comprising:
   i. a microfluidic device module for isolating nucleic acid, wherein the nucleic acid is DNA, RNA, or both, from a sample comprising a cell lysate, a bacteria-containing fluid, or a virus-containing fluid,
      wherein the microfluidic device module comprises an upper chamber, a lower chamber and a septum between the upper chamber and the lower chamber,
      wherein the upper chamber has a first input channel for receiving the sample and a second input channel for a lysis buffer,
      wherein the septum has nanopores, formed by anodization of aluminum, and is configured to retain and isolate the nucleic acid from the sample as isolated nucleic acid in the upper chamber and to allow protein from the sample to pass through the nanopores and be collected as waste in the lower chamber;
   ii. an on-chip polymerase chain reaction (PCR) module configured for receiving a droplet comprising the isolated nucleic acid,
      wherein the on-chip PCR module comprises low voltage resistive heaters, having a maximum voltage of 20 V, to create three fixed and different temperature zones for PCR thermal cycling of the isolated nucleic acid during PCR,
      wherein the low voltage resistive heaters are placed at the three vertices of an equilateral triangle to create a circular path as the circumcircle of the equilateral triangle; and
   iii. a detection unit at the on-chip PCR module for quantifying PCR products.

2. The system as claimed in claim 1, wherein the isolated nucleic acid is subjected to PCR using primers.

3. The system as claimed in claim 1, wherein a voltage of each of the low voltage resistive heaters ranges from 2 V to 20 V.

4. The system as claimed in claim 1, wherein the on-chip PCR module has a chip that contains a circuit design for the three fixed and but different temperature zones.

5. The system as claimed in claim 1, wherein the on-chip PCR module has a chip that is coated with polytetrafluoroethylene (PTFE) to minimize friction of the droplet.

6. The system as claimed in claim 1, wherein the on-chip PCR module has a chip that is directly connected to temperature controllers.

7. The system as claimed in claim 1, wherein the on-chip PCR module has a chip with dimensions of 2 cm by 2 cm.

8. The system as claimed in claim 1, wherein the on-chip PCR module has a chip that is configured to simultaneously perform PCR on multiple samples.

9. The system claimed in claim 1, wherein the isolated nucleic acid is isolated DNA that is amplified using on-chip PCR, and amplified DNA is quantified using a DNA binding fluorescent dye.

10. The system as claimed in claim 1, wherein the detection unit comprises (a) a blue light source having emissions band between 470 nm-490 nm that is coupled to a chip of the on-chip PCR module and (b) a photo diode detector with a 520 nm long pass filter.

11. The system as claimed in claim 1, wherein the system comprises neodymium magnets and a stepper motor for movement of a droplet during PCR.

12. The system as claimed in claim 1, wherein the droplet comprising the isolated nucleic acid further comprises primers, and wherein the droplet is mixed with magnetic nanomaterials to form a mixed droplet.

13. The system as claimed in claim 12, wherein the system comprises a microcontroller, a stepper motor, and neodymium magnets, and wherein the microcontroller is used to control the stepper motor to guide movement of the mixed droplet to the three fixed and different temperature zones using the neodymium magnets.

14. The system as claimed in claim 13, wherein the microcontroller is under the control of a programming code.

* * * * *